US00PP23335P2

(12) United States Plant Patent
Sparks

(10) Patent No.: US PP23,335 P2
(45) Date of Patent: Jan. 22, 2013

(54) PECAN TREE NAMED 'MORRILL'

(50) Latin Name: *Carya illinoinensis*
Varietal Denomination: Morrill

(75) Inventor: Darrell Sparks, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 48 days.

(21) Appl. No.: 13/135,572

(22) Filed: Jul. 8, 2011

(51) Int. Cl.
*A01H 5/00* (2006.01)

(52) U.S. Cl. ..... Plt./153; Plt./152

(58) Field of Classification Search ..... Plt./152, Plt./153
See application file for complete search history.

*Primary Examiner* — Susan McCormick Ewoldt
(74) *Attorney, Agent, or Firm* — Klarquist Sparkman, LLP

(57) ABSTRACT

A pecan tree distinguished by the following unique combination of characteristics: Precociousness, moderately early nut maturity, large nut size, a nut with a high percentage kernel, exceptional kernel quality, moderate resistance to scab and good resistance to powdery mildew and to black pecan aphid.

5 Drawing Sheets

Latin name of the genus and species of the plant: *Carya illinoinensis.*

Variety denomination: 'Morrill'.

BACKGROUND OF THE INVENTION

The present invention relates to a new and distinct variety of pecan tree named 'Morrill'. My new tree can be used in gardens or for commercial production of pecan nuts. This new tree was selected from seedlings grown from controlled pollination at the University of Georgia Horticulture Farm in Watkinsville, Ga., in 1989. The 'Morrill' selection resulted from crossing 'Wichita' (unpatented) as the seed parent with 'Pawnee' (unpatented) as the pollen parent. The resulting tree was selected when growing in a cultivated area at Watkinsville, Ga.

BRIEF SUMMARY OF THE INVENTION

'Morrill' is distinguished from other pecan varieties known to the inventor due to the following unique combination of characteristics: Precociousness, moderately early nut maturity, large nut size, a nut with a high kernel percentage, exceptional kernel quality, moderate resistance to scab and good resistance to powdery mildew and to black pecan aphid.

Asexual reproduction of 'Morrill' by grafting, (topworking) onto 'Kiowa' (unpatented) pecan trees in 2003 and 2007 at a location in Albany, Ga. was performed in order to evaluate these trees. Asexual propagation of 'Morrill' pecan trees has also been performed at other locations in Georgia. Asexual reproduction of 'Morrill' has shown that the forgoing characteristics come true to form, are firmly fixed, and are established and transmitted through succeeding propagations.

Certain characteristics of this variety, such as growth and color, may change with changing environmental conditions (e.g., light, temperature, moisture, nutrient availability, or other factors). Color descriptions and other terminology are used in accordance with their ordinary dictionary descriptions, unless the context clearly indicates otherwise. Color designations are made with reference to The Royal Horticultural Society (R.H.S.) Colour Chart.

Figure 1:
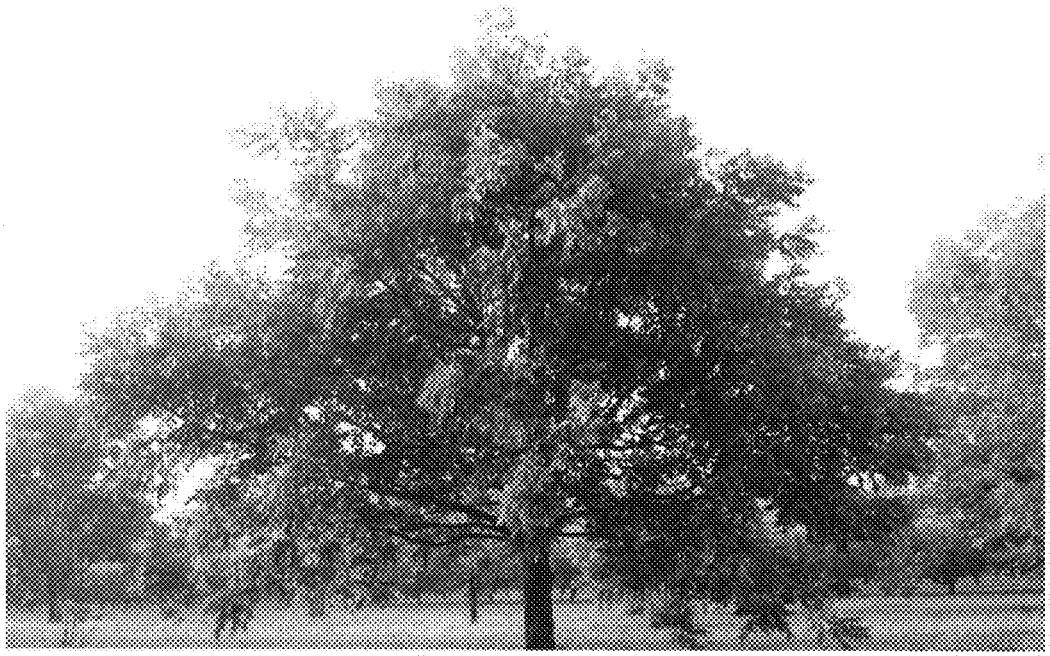
FIG. 1 is a photograph showing the original 'Morrill' tree grown from seed.
Figure 2:
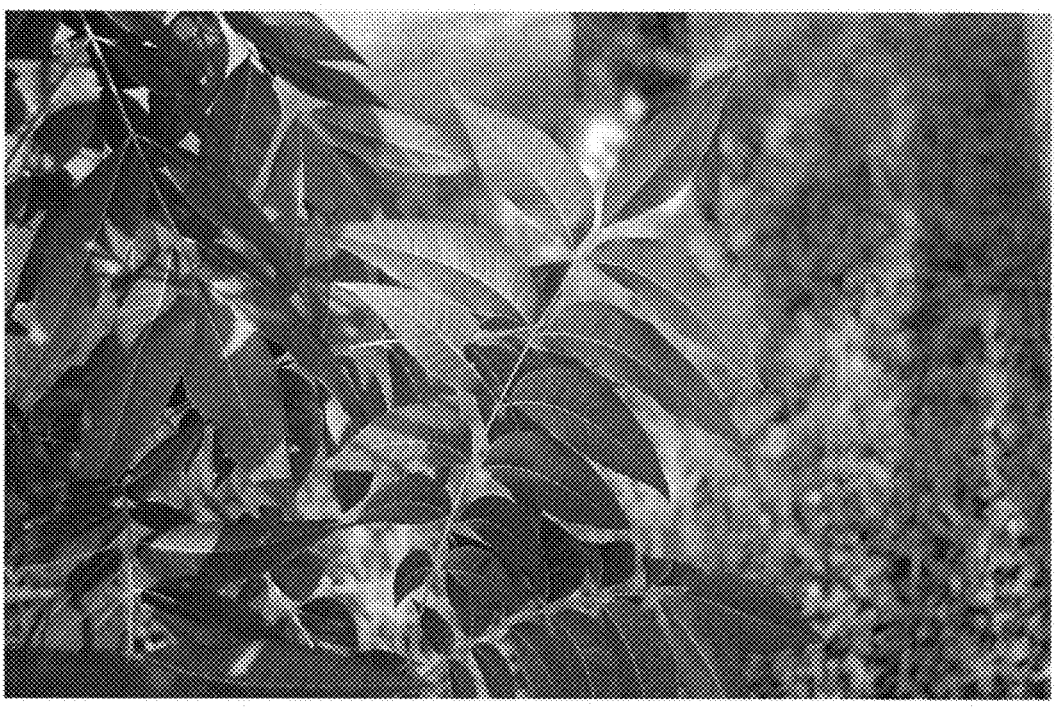
FIG. 2 is a photograph showing a number of leaves of 'Morrill'.
Figure 3:
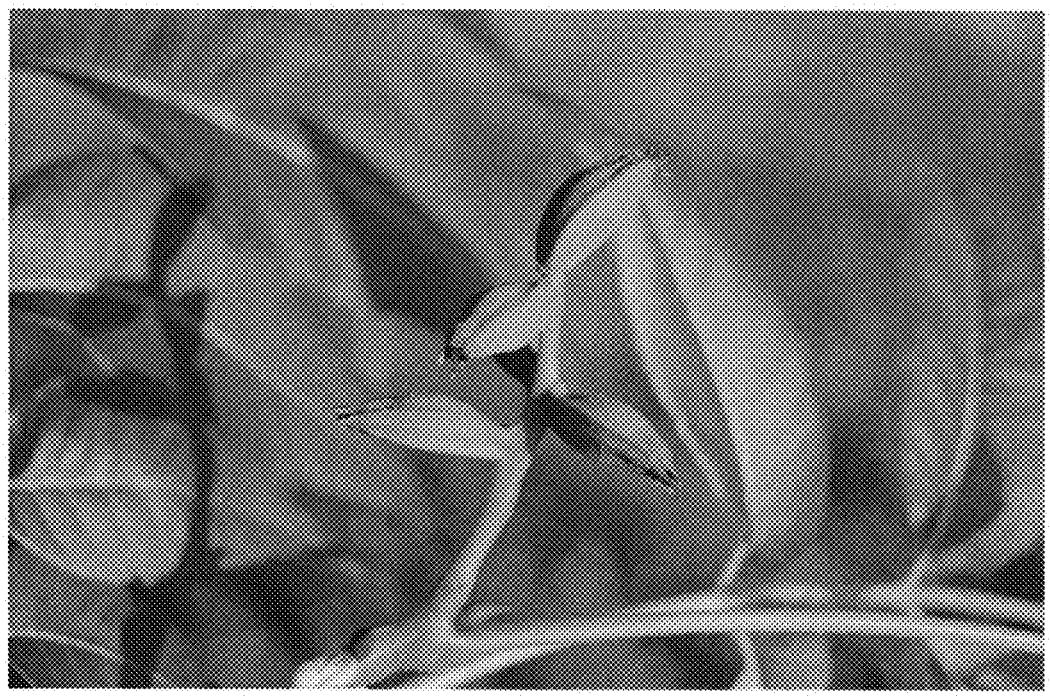
FIG. 3 is a photograph showing an immature fruit cluster of 'Morrill' pecans.
Figure 4:
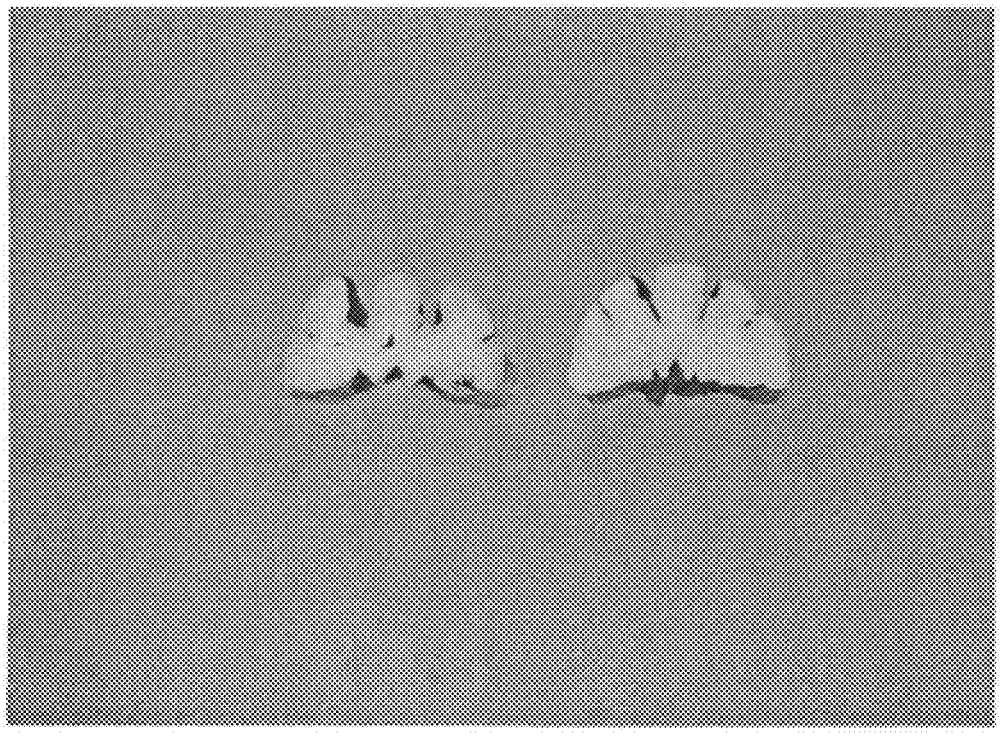
FIG. 4 is a black and white photograph showing a cross-sectional view of a nut of 'Byrd' (on the left) and a cross-sectional view of a kernel of 'Morrill' (on the right), and illustrating the narrower dorsal grooves of the 'Morrill' kernel.
Figure 5:
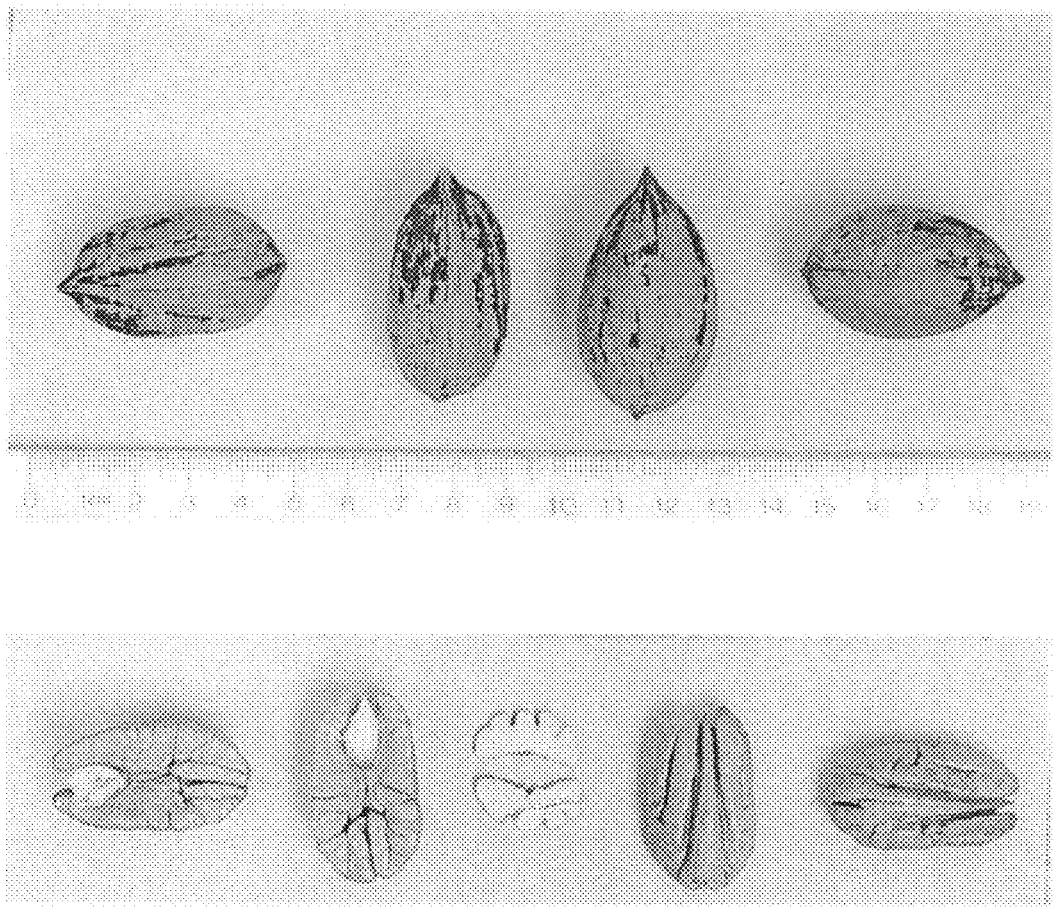
FIG. 5 is a black and white photograph showing 'Morrill' nuts in an upper portion of the photograph and 'Morrill' kernels in a lower portion of the photograph.

The colors of an illustration of this type may vary with lighting and other conditions. Therefore, color characteristics of this new variety should be determined with reference to the observations described herein, rather than from these illustrations alone.

DETAILED DESCRIPTION

BOTANICAL

The following detailed description of 'Morrill' is based on observations of the original tree growing in Watkinsville, Ga. and of asexually reproduced progeny growing in Albany, Ga.

Varietal name: 'Morrill'.

Parentage:

*Seed parent.*—'Wichita'.

*Pollen parent.*—'Pawnee'.

Tree:

*Overall shape.*—Upright, moderately spreading, height to width ratio is about 1.

*Vigor.*—Vigorous, precocious, 'Morrill' fruited the second year after grafting (topworking) onto 'Kiowa' trees, and has done so in subsequent years. Original tree fruited 10 years from seed.

*Height*.—Of original tree, about 11 meters.

*Width*.—Of overall tree, about 11 meters.

*Trunk*.—Of original tree (measured ½ meter above ground level) about 0.6 m diameter.

*Trunk bark texture*.—Fissured.

*Trunk bark color*.—Grey (RHS 202B).

*Patches*.—Trunk has no markings.

*Branch color*.—Branch shoots in woody stage are Grey-brown (RHS 199A) in color, with Grey-brown lenticels (RHS 199D) that are elongated and about 1 mm long by 0.05 mm wide.

*Internodes*.—Average internode length is about 1.3 cm, $3^{rd}$ and $4^{th}$ leaf on a shoot.

*Disease and insect resistance*.—Moderate resistance to scab (*Fusicladosporium effusum*). Good resistance to powdery mildew (*Microsphaera alni* Candolle ex Winter). Good resistance to black pecan aphid (*Melanocallis caryaefoliae*).

Leaves: The mature leaf is odd pinnate compound, deciduous with leaflets having a dark green upper surface and a lighter green lower surface. Each mature leaf has from 13 to 17 leaflets. Opposite leaflets are oriented at 180 degrees relative to each other. This flat orientation is most pronounced on basal leaflets with the leaflets becoming somewhat droopy on apical leaflets.

*Size of mature leaf* (*fourth leaf from base*).—19.8 cm long, 20.0 cm wide.

*Peduncle*.—Oval in cross-section, tan in color (RHS 199B). The length of the peduncle of the fourth leaf from the base is about 5.1 cm. The diameter of the peduncle of the fourth leaf from the base is about 2.7 mm.

*Leaflet*.—Size and shape: Fourth leaflet on fourth leaf from base 10.5 cm long by 3.3 cm wide. Eliptic in shape. Apex acuminate and narrow. Base oblique. Margin serrate. Undulation of leaflet margins is absent on basal leaves, but increases from basal to apical leaves. Texture: Smooth. Sheen: Glossy. Petiole: Sessile. Margin: Serrate. Tip shape: Acuminate. Leaflet color: Upper leaf surface: Dark green (RHS 139A). Lower leaf surface: Green (RHS 138A). Pubescence: Upper leaf surface is not pubescent. Lower surface is pubescent.

Inflorescence:

*General*.—The 'Morrill' pecan is monoecious, anemophilous, and protandrous. Dichogamy is protogynous.

*Flowers*.—Pistal flowers are born on a determinate spike, with staminate flowers born on a determinate pendulous catkin. Three-five individual pistilate flowers per spike, borne alternately on terminally-positioned spikes. The pistilate flower is symmetrical with no stamens or petals. The peticles are sessile. The staminate or catkin length is 156 mm and width is 5 mm. The staminate color is Green (RHS 144B) with gold pollen (RHS 3A). The involucre size, which includes the stigma, is 7 mm long by 1.9 mm wide. The flower has one pistil with a pink stigma. The flower has four bracts, which are green (RHS 144A), linear, lanceolate, 3.9 mm long by 0.4 mm wide and are fused at the bases, forming a copular involucre.

Fruit: Mature fruit is dehiscent.

*Shuck*.—Green (RHS 144B).

*Fruit split during water stage*.—Not observed to be a problem.

*Shuck decline*.—Shuck dieback during kernel formation has not been observed to be a problem.

Nuts: (Observations from a limited number of typical nuts from several growing seasons in Watkinsville, Ga.).

*Size*.—Large, length about 47 mm, width about 23.5 mm (width measurement taken midway along the length of the nut and across sutures); length to width ration about 2.0. Nut flatness (ratio of width across sutures to width between sutures) is about 1.1.

*Form*.—Oblong with a blunt (obtuse) base, apex that is broadly elongated and cuspidate to cuspidate asymmetric, with a grooved apex.

*Sutures*.—Subtle, non-elevated.

*Dorsal grooves*.—Narrow, thereby increasing the percentage kernel in the nut.

*Weight*.—8.7 grams per nut (non-limiting soil moisture).

*Cluster size*.—About 2.9 fruits per cluster.

*Texture*.—Subtle ridges.

*Shell thickness*.—Thin, 0.72 mm.

*Kernel color*.—Good color, Greyed-orange (RHS 165B).

*Kernel coat*.—No specking has been observed.

*Kernel percentage of nut*.—About 65.8 percent.

*Nut maturity*.—October $2^{nd}$. Later than 'Byrd' by about 13 days.

*Harvestability*.—Suitable for machine harvest.

*Cracking/shelling ability*.—Cracks exceptionally well, percentage of kernels with intact halves is high. Typically, less than five percent of chipped or broken kernels were observed.

COMPARISONS TO OTHER VARIETIES

The form of 'Morrill' trees is moderately spreading and is intermediate to its parents. Thus, 'Morrill' spreads more than its male parent 'Pawnee', which is more upright, and also more than 'Byrd'. The timing of bud break of 'Morrill' is similar to 'Stuart' and 'Pawnee' pecan trees but later than many pecan cultivars. Thus, 'Morrill' is less susceptible to late-spring freezes in Georgia than most other pecan cultivars. The leaves of 'Morrill' are dark green, but not as dark green as 'Pawnee' leaves. Leaflet orientation of 'Morrill' leaves is similar to 'Pawnee', that is, the opposite leaflet is oriented at 180 degrees relative to each other whereas leaflets of most pecan genotypes droop to varying degrees, including 'Wichita'. Undulation of leaflet margins in 'Morrill' is much more pronounced than in 'Pawnee' and is similar to leaves of 'Wichita'. The stigmatic surface of 'Morrill' is pink in contrast to the ox-blood red stigmatic of 'Pawnee' and the green surface of 'Wichita'.

Table 1 below compares periods of stigma receptivity and pollen shedding of the 'Morrill' cultivar with these characteristics of a number of other cultivars.

TABLE 1

Approximate periods of pollen shedding and stigma receptivity for 'Morrill' and other cultivars, Albany, Georgia

| | April | | | | | | | | | | May | | | | | | |
|---|---|---|---|---|---|---|---|---|---|---|---|---|---|---|---|---|---|
| | 21 | 22 | 23 | 24 | 25 | 26 | 27 | 28 | 29 | 30 | 1 | 2 | 3 | 4 | 5 | 6 | 7 | 8 |
| 'Byrd' | | | | | x | x | x | x | x | x | x | x | x | x | x | x | x | x |
| 'Desirable' | x | x | x | x | x | x | x | x | x | x | x | x | x | x | x | x | x | x |
| 'Morrill' | | | | | | | | | | | | | | | x | x | x | x |
| 'Elliott' | | | | | | | | | | | x | x | x | x | x | x | x | x |

TABLE 1-continued

Approximate periods of pollen shedding and stigma receptivity for 'Morrill' and other cultivars, Albany, Georgia

| | April | | | | | | | | | | May | | | | | | |
|---|---|---|---|---|---|---|---|---|---|---|---|---|---|---|---|---|---|
| | 21 | 22 | 23 | 24 | 25 | 26 | 27 | 28 | 29 | 30 | 1 | 2 | 3 | 4 | 5 | 6 | 7 | 8 |
| 'Kiowa' | | | | | | | ..... | | | | xxxxxxxx | | | | | | | |
| 'Stuart' | | | | | | | | ..... | | | | | | | xxxxxxxxxxxxx | | | |

..... = Period of stigma receptivity.
xxxxxxx = Period of pollen shedding.

Tables 2 and 3 below compare the characteristics of nuts from 'Morrill' with nuts of other pecan cultivars.

TABLE 2

Comparison of nut characteristics of 'Byrd', 'Pawnee' and 'Morrill' pecan cultivars, Watkinsville, Georgia

| Cultivar | Volume/nut (cc) | Wt./nut (g) | Nut length (mm) | Length/width[z] | Nut Flatness ratio[y] | Shell thickness (mm) | Kernel (%) | Nut Maturity date[x] |
|---|---|---|---|---|---|---|---|---|
| 'Byrd' | 11.3a | 7.8a | 42.5a | 1.87c | 1.04b | 0.65c | 61.9b | 9/19b |
| 'Pawnee' | 10.9a | 7.6a | 41.9a | 1.95b | 0.96c | 0.77a | 59.3c | 9/18b |
| 'Morrill' | 12.0a | 8.7a | 47.1b | 2.01a | 1.11a | 0.72b | 65.8a | 10/2a |

Means followed by the same letter within a column are not statistically different, P ≧ 0.05.
[z]Length to width ratio = nut length divided by width. Width was measured midway the length of the nut and across sutures.
[y]Nut flatness ratio = ratio of nut width across sutures to width between sutures.
Measurements were made midway the length of the nut.
[x]Nut maturity date of 'Desirable' is October 15.

TABLE 3

Nut characteristics of 'Byrd' and 'Morrill', Albany, Georgia

| Cultivar | Wt./nut (g) | Nuts/lb. (no.) | Kernel (%) |
|---|---|---|---|
| 'Byrd' | 9.6a | 47a | 63.5a |
| 'Morrill' | 9.8a | 46a | 67.4b |

Means followed by the same letter within a column are not statistically different, P ≧ 0.05.
Greater nut size and percentage kernel in Albany, Georgia as compared to Watkinsville, Georgia (Table 2) believed due to better irrigation and probably higher temperatures in Albany, Georgia. Soil water was non-limiting at Albany, but not at Watkinsville.

Pecan nuts of large size that mature relatively early command a premium price. The price per pound normally declines as the harvest becomes later. Consequently, cultivars that exhibit early maturity at harvest are commercially important. The color of a kernel's seed coat (lighter is preferred), and the percentage kernel of the nut also affects the selling price of pecans. Although the nut maturity of 'Morrill' is about 13 days later than nut maturity of 'Byrd', it is about 13 days earlier than the 'Desirable' cultivar (unpatented). 'Desirable' is believed to be the leading cultivar now being planted in new orchards in Georgia. Although the nut maturity of 'Morrill' is later than 'Byrd', the maturity date is still early enough to be considered an early market cultivar. The later harvest date of 'Morrill' is advantageous in one respect because a number of growers of pecans in southwest Georgia also grow peanuts. The harvest date of 'Byrd' pecan trees conflicts with the peanut harvest date. 'Morrill' matures at the end of the peanut harvesting season, making it a more suitable early cultivar for peanut growers that can harvest 'Morrill' pecans following the peanut harvest.

As can be seen from Table 2, the nut volume and weight of 'Morrill' nuts are substantially same as those of 'Pawnee' and 'Byrd'. However, the nut length is longer in the case of 'Morrill' nuts than either 'Pawnee' or 'Byrd' nuts and the nut shape differs. As indicated by the length to width ratio, 'Morrill' nuts are more oblong than 'Pawnee' or 'Byrd' nuts. In cross-section, 'Byrd' nuts are near round (flatness ratio 1.04) while 'Pawnee' nuts are flatter on the suture side than the non-suture side. In contrast, 'Morrill' nuts are flatter on the non-suture side than the suture side. Referring to Table 2, the shell thickness of 'Morrill' is intermediate between the shell thickness of 'Byrd' and 'Pawnee'. All three have unusually thin shells, which accounts, in part, for their high percentage kernel. However, the percentage kernel of 'Morrill' nuts is substantially higher than 'Byrd' nuts even though the shells of 'Byrd' nuts are thinner. The higher percentage kernel of 'Morrill' is due in part to the differences in the morphology of the dorsal grooves in 'Morrill' in comparison to 'Byrd'. The dorsal grooves are deep and wide in 'Byrd', but much narrower in 'Morrill', thereby increasing the percentage kernel in the nut of 'Morrill' nuts. The percentage kernel is a direct function of the shell thickness and the percentage of the shell cavity filled with the kernel.

The percentage kernel of 'Morrill' nuts, as can be seen from Table 2, is high and is substantially higher than any existing pecan cultivar known to the inventor.

Under stress, primarily fruiting stress, when 'Pawnee' cultivar pecan trees are grown in humid southeastern United States markets such as Georgia, the kernel seed coats of nuts can develop conspicuous and unattractive dark spots. This specking reduces the marketability of these nuts. Specking has not been observed to be a problem of 'Morrill' nuts grown in Georgia. In addition, unlike the 'Morrill' cultivar, during a heavy "on" nut production year for 'Pawnee' trees growing in Georgia, kernel development is relatively poor, resulting in a high percentage of the nuts being unmarketable or of reduced value.

Table 4 below compares the fruiting characteristics of 'Morrill' and 'Byrd' cultivars.

TABLE 4

Fruiting characteristics of 'Byrd' and 'Morrill', Albany, Georgia

| Cultivar | Years to fruiting[z] (no.) | Years until alternate bearing[z] (no.) |
|---|---|---|
| 'Byrd' | 2 | 3 |
| 'Morrill' | 2 | >5 |

[z]Years after topworking mature trees to the respective cultivar.

As apparent from Table 4, the 'Morrill' variety is precocious. Both 'Morrill' and 'Byrd' fruited two years after topworking onto older 'Kiowa' pecan trees. It does not appear 'Morrill' is as precocious as 'Byrd' as indicated by the onset of alternate bearing in 'Byrd' trees the third year from topworking in contrast to alternate bearing in 'Morrill' trees having not occurred by the fifth year. Also, the original 'Morrill' tree bore its first fruit the tenth year from planting as seed. In comparison, the original tree of 'Byrd' first fruited the seventh year from planting as seed.

As indicated in Table 5 below, the cluster size of 'Morrill' and 'Byrd' is about the same. It does appear that 'Morrill' has lower density of fruiting shoots than 'Byrd'. Because of 'Morrill's precocity, large nut size and large cluster size, it is expected to bear alternately with increasing tree maturity as occurs with most pecan cultivars including its parent trees, 'Wichita' and 'Pawnee'.

TABLE 5

Fruit cluster size of 'Byrd', 'Desirable', 'Morrill' and 'Pawnee', Watkinsville, Georgia

| Cultivar | Fruit/cluster (no.) | SD | CV |
|---|---|---|---|
| 'Byrd' | 3.1a | 0.68 | 22 |
| 'Desirable' | 1.8b | 0.59 | 34 |
| 'Morrill' | 2.9a | 0.83 | 28 |
| 'Pawnee' | 3.1a | 0.83 | 26 |

Means followed by the same letter are not statistically different, P ≧ 0.05.
SD = Standard deviation
CV = Coefficient of variation Table 6 below compares scab and powdery mildew susceptibility of 'Morrill' with 'Byrd' and 'Desirable'. In addition, 'Pawnee' has been observed to be more susceptible to scab disease than 'Morrill' when grown in Georgia. 'Wichita', when grown in Georgia's humid climate, is highly susceptible to scab fungus.

TABLE 6

Fruit scab and powdery mildew susceptibility of 'Byrd', 'Desirable' and 'Morrill'

| Cultivar | Fruit scab[z] | Powdery mildew[y] |
|---|---|---|
| 'Byrd' | 1.6 | 2 |
| 'Desirable' | 5.0 | 3 |
| 'Morrill' | 2.5 | 2 |

[z]= no scab; 2 = very slight and occasional lesions on fruit, <10% of fruits with scab; 3 = lesions common on fruit by not damaging, 11-50% of fruits with scab; 4 = widespread lesions on fruit but not damaging, 51-75% of fruits with scab; 5 = widespread and damaging lesions on fruit, fruit size suppressed and nut is non-marketable. Ratings from NILO Plantation and were made in 2005 a major scab season.
[y]= no mildew, 2 = < than 5% of the fruit covered with mildew, 3 = 6-25% covered, 4 = 26-50% covered, 5 = 51-100% covered. Ratings from Watkinsville and were made in 2008.

Table 7 below compares the black pecan aphid resistance of 'Morrill' to the resistance of two other cultivars.

TABLE 7

Black pecan aphid susceptibility of 'Byrd', 'Sumner' and 'Morrill', Leary, Georgia

| Cultivar | Black pecan aphid[y] |
|---|---|
| 'Byrd' | 1.0a |
| 'Sumner'[z] | 1.8b |
| 'Morrill' | 1.0a |

Means followed by the same letter are not statistically different, P ≧ 0.05.z
[z]During a heavy infestation 'Sumner' (unpatented) is highly susceptible to black pecan aphid.
[y]1 = no leaf damage, 2 = <1% of leaves with injury, 3 = 1-10% of leaves with injury, 4 = 11-50% of leaves with injury, 5 = >51% of leaves with injury and partial defoliation.
Data taken during a year of low aphid population.

In addition, under these humid growing conditions in Georgia, the fruit is highly susceptible to splitting during the "water stage" (liquid endosperm stage) of fruit development. Fruit split can occur following rain and accompanying high humidity in early August in Georgia. Although 'Wichita' has a relatively early nut maturity (7-10 days before 'Stuart') and acceptable nut size (57 nuts per pound), and a kernel percentage of 60-61%, which is higher than the 58-59% of 'Pawnee', because of the susceptibility to scab fungus and splitting it has become a less desirable cultivar for growing in Georgia. Water split has not been observed in 'Morrill'. The lack of split may be due to the timing of fruit development. Water split is most likely to occur on cultivars when the maximum liquid endosperm stage occurs during the first two weeks in August that often coincides with the rainy period in Georgia. Typically, rainfall in Georgia sharply decreases after August 15th. The maximum liquid endosperm stage in 'Morrill' trees grown in Georgia occurs after August 15th.

The 'Morrill' pecan tree is therefore an improved new and distinct pecan.

I claim:

1. A new and distinct cultivar of pecan tree, substantially as herein shown and described.

* * * * *

UNITED STATES PATENT AND TRADEMARK OFFICE

CERTIFICATE OF CORRECTION

PATENT NO. : PP23,335 P2
APPLICATION NO. : 13/135572
DATED : January 22, 2013
INVENTOR(S) : Darrell Sparks It is certified that error appears in the above-identified patent and that said Letters Patent is hereby corrected as shown below:

In the Specification:

Replace Table 1 beginning at line 55, with the following Table 1:

TABLE 1

Table 1. Approximate periods of pollen shedding and stigma receptivity for 'Morrill' and other cultivars, Albany, Georgia

| | April | | | | | | | | | | May | | | | | | | |
|---|---|---|---|---|---|---|---|---|---|---|---|---|---|---|---|---|---|---|
| | 21 | 22 | 23 | 24 | 25 | 26 | 27 | 28 | 29 | 30 | 1 | 2 | 3 | 4 | 5 | 6 | 7 | 8 |
| 'Byrd' | | | | | xxxxxxxxxxxxxxxxxxxx | | | | ..... | | | | | | | | | |
| 'Desirable' | | | xxxxxxxxxxxxxxxxxxxxxx | | | | | ..... | | | | | | | | | | |
| 'Morrill' | | | | | | | | | | | ..... | | | xxxxxxxxxxxxxxxxx | | | | |
| 'Elliott' | | | | | ..... | | | | | | xxxxxxxxxxxxxxxxxxxxxxxxxx | | | | | | | |
| 'Kiowa' | | | | | ..... | | | | xxxxxxxxxxxxx | | | | | | | | | |
| 'Stuart' | | | | | | | ..... | | | | | | | xxxxxxxxxxxxxxxxxxxxxxx | | | | |

..... = Period of stigma receptivity.
xxxxxxx = Period of pollen shedding.

Signed and Sealed this
Fourteenth Day of October, 2014

Michelle K. Lee

Michelle K. Lee
*Deputy Director of the United States Patent and Trademark Office*

UNITED STATES PATENT AND TRADEMARK OFFICE

CERTIFICATE OF CORRECTION

PATENT NO. : PP23,335 P2
APPLICATION NO. : 13/135572
DATED : January 22, 2013
INVENTOR(S) : Darrell Sparks It is certified that error appears in the above-identified patent and that said Letters Patent is hereby corrected as shown below:

In the Specification:

Replace Table 1 beginning at Column 4, line 55 - Column 5, line 12, with the following Table 1:

TABLE 1

Table 1. Approximate periods of pollen shedding and stigma receptivity for 'Morrill' and other cultivars, Albany, Georgia

| | April | | | | | | | | | | May | | | | | | | |
|---|---|---|---|---|---|---|---|---|---|---|---|---|---|---|---|---|---|---|
| | 21 | 22 | 23 | 24 | 25 | 26 | 27 | 28 | 29 | 30 | 1 | 2 | 3 | 4 | 5 | 6 | 7 | 8 |
| 'Byrd' | | | | | xxxxxxxxxxxxxxxxxxxxx | | | | | ..... | | | | | | | | |
| 'Desirable' | | | xxxxxxxxxxxxxxxxxxxxxxx | | | | | ..... | | | | | | | | | | |
| 'Morrill' | | | | | | | | | | | ..... | | | xxxxxxxxxxxxxxxxxx | | | | |
| 'Elliott' | | | | ..... ..... ... | | | | | | | xxxxxxxxxxxxxxxxxxxxxxxxxxx | | | | | | | |
| 'Kiowa' | | | | ..... | | | | | xxxxxxxxxxxxx | | | | | | | | | |
| 'Stuart' | | | | | | | ..... | | | | | | xxxxxxxxxxxxxxxxxxxxxxxx | | | | | |

..... = Period of stigma receptivity.
xxxxxxx = Period of pollen shedding.

This certificate supersedes the Certificate of Correction issued October 14, 2014.

Signed and Sealed this
Eleventh Day of November, 2014

Michelle K. Lee

Michelle K. Lee
*Deputy Director of the United States Patent and Trademark Office*